US012679805B2

(12) United States Patent
Osada et al.

(10) Patent No.: US 12,679,805 B2
(45) Date of Patent: Jul. 14, 2026

(54) BIOACTIVE SUBSTANCE EXHIBITING ANTIMALARIAL ACTIVITY, AND USE FOR SAME

(71) Applicant: RIKEN, Wako (JP)

(72) Inventors: Hiroyuki Osada, Saitama (JP); Takayuki Motoyama, Saitama (JP); Islam Adel Abdelhakim, Assiut (EG); Yushi Futamura, Saitama (JP)

(73) Assignee: RIKEN, Saitama (JP)

( * ) Notice: Subject to any disclaimer, the term of this patent is extended or adjusted under 35 U.S.C. 154(b) by 333 days.

(21) Appl. No.: 18/278,325

(22) PCT Filed: Mar. 3, 2022

(86) PCT No.: PCT/JP2022/009098

§ 371 (c)(1),
(2) Date: Aug. 22, 2023

(87) PCT Pub. No.: WO2022/186328

PCT Pub. Date: Sep. 9, 2022

(65) Prior Publication Data

US 2024/0190818 A1 Jun. 13, 2024

(30) Foreign Application Priority Data

Mar. 4, 2021 (JP) ................................ 2021-034047

(51) Int. Cl.
*C07D 207/273* (2006.01)
*A61K 31/4015* (2006.01)
*A61P 33/06* (2006.01)

(52) U.S. Cl.
CPC ...... *C07D 207/273* (2013.01); *A61K 31/4015* (2013.01); *A61P 33/06* (2018.01)

(58) Field of Classification Search
CPC .. C07D 207/273; A61P 33/06; A61K 31/4015
USPC .......................................................... 514/423
See application file for complete search history.

(56) References Cited

FOREIGN PATENT DOCUMENTS

JP 4808853 B2 11/2011

OTHER PUBLICATIONS

Abdelhakim et al., "Dihydrolucilactaene, a Potent Antimalarial Compound from *Fusarium* sp. RK97-94," Journal of Natural Products, 2022 (Dec. 24, 2021), 85(1):63-69.
Hayashi et al., "Asymmetric Total Synthesis of Epolactaene," Chemistry Letters, 1998, 313-314.
Hayashi et al., "The diastereoselective asymmetric total synthesis of NG-391, a neuronal cell-protecting molecule," Tetrahedron, 2002, 58:9839-9846.
International Search Report dated Apr. 19, 2022 in PCT/JP2022/009098.
Kato et al., "Biosynthetic gene cluster identification and biological activity of lucilactaene from *Fusarium* sp. RK97-94," Bioscience, Biotechnology, and Biochemistry, 2020, 84(6):1303-1307.
Yamaguchi et al., "Determination by Asymmetric Total Synthesis of the Absolute Configuration of Lucilactaene, a Cell-Cycle Inhibitor in p53-Transfected Cancer Cells," Angew. Chem. Int. Ed., 2005, 44:3110-3115.
Yamaguchi et al., "The Asymmetric Total Synthesis of Lucilactaene, a Cell Cycle Inhibitor in p53-Transfected Cancer Cells," 47th Symposium on the Chemistry of Natural Products, symposium papers, 2005, with English abstract.

*Primary Examiner* — Kahsay Habte
(74) *Attorney, Agent, or Firm* — Foley & Lardner LLP

(57) ABSTRACT

The present invention relates to a compound represented by the following formula (I):

[Formula 1]

(I)

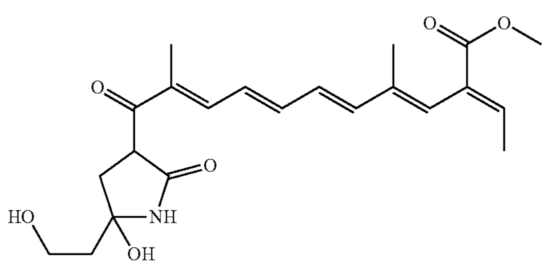

and an antimalarial drug comprising the compound.

2 Claims, 1 Drawing Sheet

DHLC vs 3D7 (WT) and K1 (CQ-resistant)
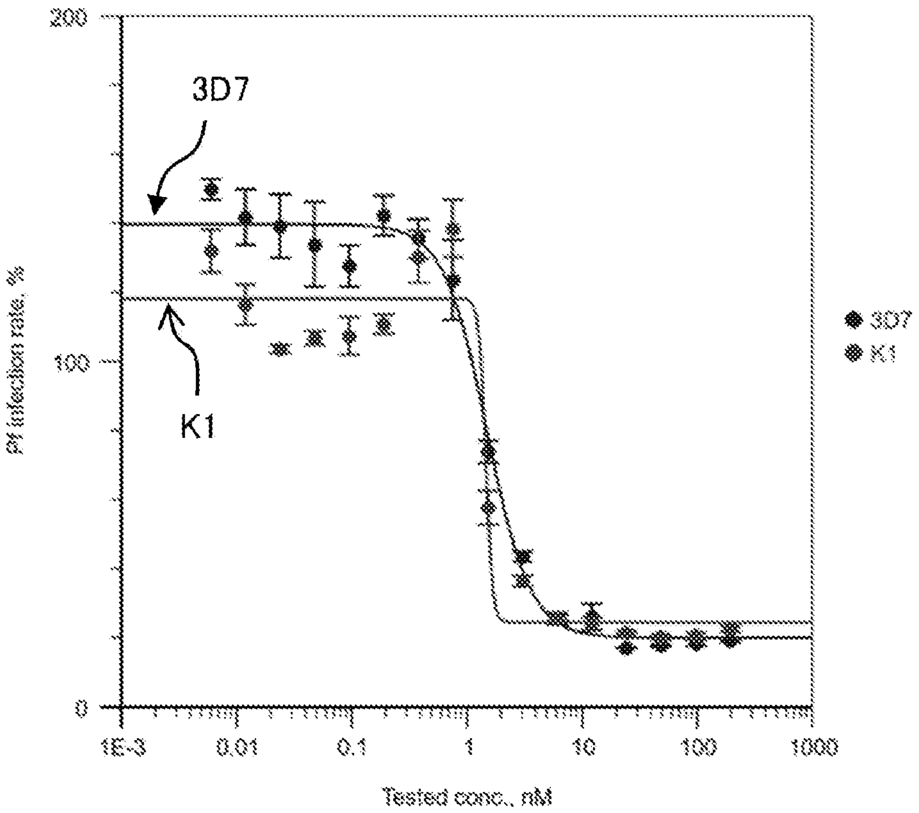

BIOACTIVE SUBSTANCE EXHIBITING ANTIMALARIAL ACTIVITY, AND USE FOR SAME

CROSS-REFERENCE TO RELATED APPLICATIONS

This application is the U.S. National Stage of PCT/JP2022/009098, filed Mar. 3, 2022, which claims priority to JP 2021-034047, filed Mar. 4, 2021.

TECHNICAL FIELD

The present invention relates to a novel bioactive substance exhibiting antimalarial activity and the use thereof.

BACKGROUND ART

Malarial parasites, which are parasitic in humans, are classified into five types: *Plasmodium falciparum, P. vivax, P. malariae, P. ovale* and *P. knowlesi*. Of them, the most troublesome parasite is *Plasmodium falciparum*, which is a cause of approximately 80% of the malaria patients. Patients with severe symptoms result in death.

Although effective antimalarial drugs have been developed, a drug-resistant malarial parasite has emerged, which has acquired resistance against a drug due to a mutation in a target protein (ATP4) for a conventional antimalarial drug, and become a threat in infected areas. Thus, in recent years, particularly the development of an antimalarial drug having an effect on drug-resistant malaria has been desired.

The present inventors found that lucilactaene contained in a secondary metabolite of a filamentous fungus, *Fusarium* sp. RK97-94 strain (*Fusarium* sp. RK97-94) has high antimalarial activity ($IC_{50}$: 0.063 μg/ml) against *Plasmodium falciparum* and reported the finding in the paper published (Non Patent Literature 1).

Lucilactaene is a compound having a two-ring heterocyclic structure, which is formed by the condensation of a tetrahydrofuran ring and a γ-lactam ring, and is represented by the following formula (A):

[Formula 1]

(A)

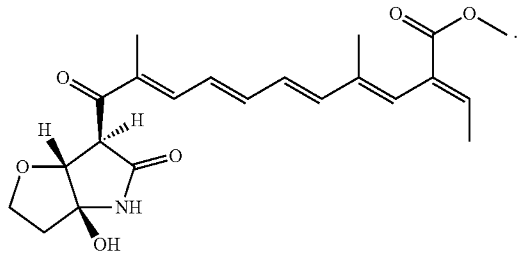

Lucilactaene has been totally synthesized (Non Patent Literatures 2 to 5).

Patent Literature 1 discloses that lucilactaene has an antitumor activity and that the accession number of *Fusarium* sp. RK97-94 strain is IPOD FERM P-18143.

CITATION LIST

Patent Literature

Patent Literature 1: JP Patent No. 4808853

Non Patent Literatures

Non Patent Literature 1: BIOSCIENCE, BIOTECHNOLOGY, AND BIOCHEMISTRY 2020, VOL. 84, NO. 6, 1303-1307 (https://doi.org/10.1080/09168451.2020.1725419)

Non Patent Literature 2: Chem. Lett. 1998, 313-314 (https://www.journal.csj.jp/doi/10.1246/cl.1998.313)

Non Patent Literature 3: Tetrahedron 58 (2002) 9839-9846 (The diastereoselective asymmetric total synthesis of NG-391, a neuronal cell-protecting molecule)

Non Patent Literature 4: Angew. Chem. Int. Ed. 2005, 44, 3110-3115 (Determination by Asymmetric Total Synthesis of the Absolute Configuration of Lucilactaene, a Cell-Cycle Inhibitor in p53-Transfected Cancer Cells)

Non Patent Literature 5: 47th Symposium on the Chemistry of Natural Products, symposium papers (2005), 5 Consideration of asymmetric total synthesis and biosynthesis of lucilactaene having antitumor activity (https://doi.org/10.24496/tennenyuki.47.0_25)

SUMMARY OF INVENTION

Technical Problem

An object of the present invention is to provide a novel antimalarial drug providing a high effect even at a low concentration and having an effect on drug-resistant malaria.

Solution to Problem

The present inventors conducted various studies on a secondary metabolite by *Fusarium* sp. RK97-94 strain with a view to attaining the object. As a result, they found that the secondary metabolite contains a compound exhibiting antimalarial activity 100 times or more as high as lucilactaene. They isolated the compound and analyzed its structure. As a result, they found that the compound has a structure obtained by opening a tetrahydrofuran ring in a two-ring heterocyclic structure of lucilactaene. Based on the finding, they arrived at the achievement of the present invention.

More specifically, the gist of the present invention is as follows.

(1) A compound represented by the following formula (I):

[Formula 2]

(I)

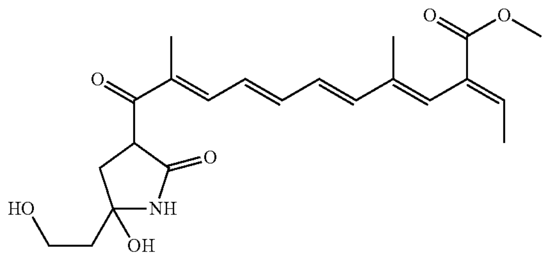

(2) An antimalarial drug comprising the compound according to (1).

Advantageous Effects of Invention

According to the present invention, it is possible to provide a novel antimalarial drug providing a high effect even at a low concentration and having an effect on drug-resistant malaria.

BRIEF DESCRIPTION OF DRAWING

FIG. 1 shows the evaluation results of antimalarial activity.

DESCRIPTION OF EMBODIMENTS

A compound represented by formula (I) has a chiral carbon. Due to the presence of the chiral carbon, the compound has a stereoisomer such as an optical isomer or a diastereomer. Not only stereoisomers having stereochemically pure form but also a mixture of stereoisomers or a racemate fall within the scope of the present invention. The compound of the present invention has five olefinic double bonds. Geometric isomers based on each of the double bonds may exist. Not only geometric isomers having pure form but also a mixture of geometric isomers fall within the scope of the present invention. Further, the compound of the present invention may sometimes present as a tautomer. A tautomer or a mixture thereof falls within the scope of the present invention. The compound of the present invention can be present in a crystal form and sometimes as a hydrate or a solvate. Needless to say, any substances fall within the scope of the present invention.

In the specification, the compound represented by formula (I) is sometimes called as "DHLC". Note that, since stereoisomers (or geometric isomers) of the compound are partly present in equilibrium, formula (I) represents a major one of stereoisomer thereof. When the predetermined stereoisomer is subjected to a separation/purification means such as high-performance liquid chromatography to convert into a stereochemically pure form, equilibrium with other stereoisomers (or geometric isomers) is quickly obtained.

The compound represented by formula (I) can be produced by culturing a fungus producing the compound and belonging to the genus *Fusarium*. Examples of the fungus producing the compound and belonging to the genus *Fusarium* include *Fusarium* sp. RK97-94 strain, which is a microorganism separated from the soil collected around Mt. Inasayama, Nagasaki city, Nagasaki prefecture, Japan. The microorganism has been deposited under accession number IPOD FERM P-18143 in the International Patent Organism Depositary (IPOD) and disclosed in many documents including Patent Literature 1 and Non Patent Literature 1.

*Fusarium* sp. RK97-94 strain has been deposited for JP Patent No. 4808853 (Patent Literature 1) on lucilactaene. The term of the patent right has already expired. *Fusarium* sp. RK97-94 strain has been deposited at the Japan Collection of Microorganisms, RIKEN BioResource Research Center (JCM, 3-1-1 Koyadai, Tsukuba city, Ibaraki prefecture, Japan). The microorganism is available upon request and based on depositor's consent is obtained.

The compound represented by formula (I) can be preferably produced by separating/collecting it from a culture of *Fusarium* sp. RK97-94 strain. A method for separating/collecting the compound is not particularly limited and a method as disclosed in Examples later described can be preferably employed; for example, by culturing a fungus belonging to the genus *Fusarium* in accordance with a method commonly employed to obtain a culture solution, and subjecting the culture solution to usual separation/purification means to obtain the compound of the present invention. After completion of the culture, the compound of the present invention can be separated/isolated from the culture solution, appropriately by means commonly used for collecting a microbial metabolite. Examples of the means include centrifugation, extraction with a solvent, various ion exchange resins, nonionic adsorption resins, gel filtration chromatography, chromatographic means using an adsorbent such as activated carbon, alumina or silica gel, high-performance liquid chromatography, or means such as crystallization, vacuum concentration or lyophilization. These means can be used alone or appropriately in combination. Alternatively, a single means is repeatedly used.

Lucilactaene represented by formula (A) is totally synthesized (Non Patent Literatures 2 to 5). The compound represented by formula (I) can be obtained by converting a compound, which is obtained during the process for totally synthesizing lucilactaene and described in Examples later described. Thus, the compound represented by formula (I) can also be totally synthesized without using the microorganism as mentioned above.

The compound of the present invention represented by formula (I) is useful as an antimalarial drug. The administration method, dosage form and dose of an antimalarial drug containing the compound of the present invention as an active ingredient can be appropriately determined depending on the intended use. For example, the administration mode of the antimalarial drug containing the compound of the present invention as an active ingredient may be either the oral or the parenteral route. Examples of the dosage forms include oral dosage forms such as tablets, powders, capsules, granules, extracts and syrups; or parenteral dosage forms such as injections, drips and suppositories. These pharmaceutical preparations can be produced by using pharmaceutically acceptable additives such as an excipient or binder in accordance with a method commonly known in the art. The dose of the antimalarial drug containing the compound of the present invention as an active ingredient varies depending on the age, body weight, sensibility, degree of severity and the like of the patient. The effective dose is usually about 0.1 mg to 1 g per adult per day and can be administered once a day or several times by dividing the dose into several portions. If necessary, the dose outside the range mentioned above can be used.

This description includes part or all of the content as disclosed in the description and/or drawing of Japanese Patent Application No. 2021-034047, which is a priority document of the present application.

EXAMPLES

Hereinafter, the present invention will be more specifically described by way of Examples but the scope of the present invention is not limited to these Examples.

(Example 1) Production of the Compound of the Present Invention Using Microorganism

(1) Culture

*Fusarium* sp. RK97-94 strain (Kakeya, H. et al. Lucilactaene, a new cell cycle inhibitor in p53-transfected cancer cells, produced by a *Fusarium* sp. [2]. Journal of Antibiotics (2001) doi: 10.7164/antibiotics.54.850) was used as a parent fungus. The strain was provided by the Chemical Biology Research Group, National Research and Development Agency, RIKEN Center for Sustainable Resource Science (Chemical biology research building, 2-1, Hirosawa, Wako city, Saitama prefecture, Japan).

For purifying a novel lucilactaene-related compound, a culture (5 L) of *Fusarium* sp. RK97-94 strain was prepared by use of 12 flasks (2 L/per flask). Each of the flasks contained 425 ml of a culture (YG medium 416 ml (5% of yeast extract and 2% of glucose) and 8 ml of fungal preculture, 400 μl of 30 mM NPD938), and was cultured statically at 28° C. for 10 days.

(2) Purification (a) Fractionation by Preparative Medium-Pressure Liquid Chromatography (MPLC)

The culture in the flasks was extracted with the same volume of acetone, overnight. The extract was filtered and the acetone layer was concentrated under vacuum. Then, the water layer was fractionated with the same volume of anhydrous ethyl acetate three times. After ethyl acetate was evaporated off to obtain 2.77 g of a dark reddish-brown oily residue. The extract was fractionated by normal-phase MPLC using gradient elution of hexane (solvent A) and ethyl acetate (solvent B) (B 10%, 3 CV (column volume); B 20%, 3 CV; B 20 to 50%, 15 CV; B 50 to 100%, 15 CV; and then, washing with 100% ethyl acetate, 3 CV and 100% methanol, 5 CV).

(b) Isolation of Metabolite Induced

Fractions 64 to 72 of the MPLC fractionation tube were collected (about 400 mg), dissolved in 5 ml of methanol and subjected to preparative high-performance liquid chromatography using a reverse-phase column (PEGASIL ODS, 20×250 mm, 5 μM, Senshu Science Co., Ltd.). In this manner, the fractions were further fractionated into 4 sub-fractions (I, II, III and IV).

Mobile phase: A (0.05% formic acid/water), B (acetonitrile), gradient elution: B 40 to 60% (0 to 40 minutes), B 60 to 100% (40 to 50 minutes), B 100% (50 to 60 minutes); flow rate 9 ml/minute.

A compound (1) (hereinafter referred to also as "DHNG") was accumulated in sub-fraction I (80 mg). Sub-faction I was subjected to semi-preparative high-performance liquid chromatography in the same manner as above (PEGASIL ODS, 10×250 mm, 5 μM, Senshu Science Co., Ltd., flow rate 4 ml/minute), and then, to a silica open-tube column using a chloroform and methanol gradient elution (methanol 0, 2.5, 5, 10, 50%) to obtain 3.5 mg of compound (1). The compound (1) was obtained as two isomers mutually converting. These isomers had a tendency of equilibrating in a ratio of 1:4.

In fractions 73 to 77 (65 mg) of an MPLC fractionation tube, compound (2) (hereinafter referred to also as "DHLC") was accumulated. The compound (2) had the same retention time as NG-391 and the like, as disclosed in Non Patent Literature 1 (BIOSCIENCE, BIOTECHNOLOGY, AND BIOCHEMISTRY 2020, VOL. 84, NO. 6, 1303-1307) but a different mass value ($[M+H]^+$ 404.3 m/z) from NG-391 and the like. Using a silica open-tube column, a chloroform and methanol gradient elution (methanol 0, 2.5, 5, 10, 50%) was carried out to obtain fractions 6 and 7 (4.2 mg) containing the compound (2). Further, the fractions were purified similarly by semi-preparative high-performance liquid chromatography using a reverse-phase column, in the absence of formic acid at a flow rate of 4 ml/minute, separately collected in airtight opaque flasks placed in an ice box, and lyophilized to obtain the compound (2) (1.2 mg in total).

(3) Determination of Structure (a) Compound (1)

The physicochemical properties of the compound (1) are shown below.

Nature: yellow oil

Molecular formula: $C_{22}H_{29}NO_7$

Analysis by high resolution mass spectrometry (HR-ESI-TOF-MS): $[M+Na]^+$ 442.18229 m/z; $[M-H]^-$ 418.18452 m/z NMR data ($^1H$ NMR (500 MHz), $^{13}C$ NMR (125 MHz)): shown in Table 1.

The physicochemical properties were compared to those of NG-391 and lucilactaene whose structures are already known in the art. As a result, it was determined that the compound (1) (DHNG) has the following structure.

[Formula 3]

Compound (1)

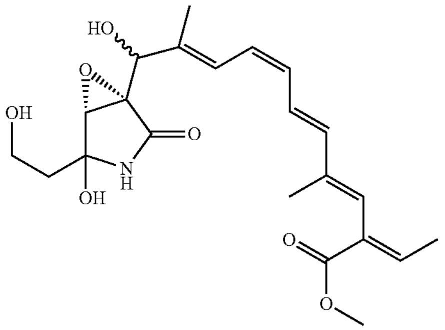

(b) Compound (2)

The physicochemical properties of the compound (2) are shown below.

Nature: yellow amorphous powder

Molecular formula: $C_{22}H_{29}NO_6$

Analysis by high resolution mass spectrometry (HR-ESI-TOF-MS): $[M+Na]^+$ 426.18897 m/z; $[M-H]^-$ 402.19148 m/z NMR data ($^1H$ NMR (500 MHz), $^{13}C$ NMR (125 MHz)): shown in Table 1.

The physicochemical properties were compared to those of NG-391, lucilactaene and DHNG whose structures are already known in the art. As a result, it was determined that the compound (2) (DHLC) has the following structure.

[Formula 4]
Compound (2)
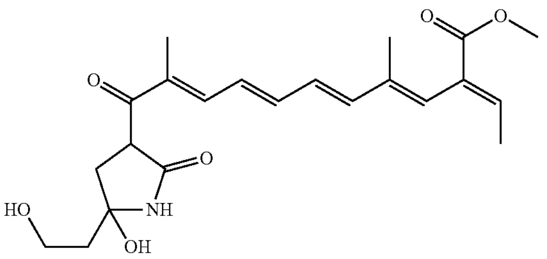
TABLE 1
| | DHNG (1) | | | | DHLC-1 (2) | | | |
|---|---|---|---|---|---|---|---|---|
| No. | $\delta_H$ (Multiplicity, J Hz) | $\delta_C$ Type | HMBC | NOESY | $\delta_H$ (Multiplicity, J Hz) | $\delta_C$ Type | HMBC | NOESY |
| 1 | 1.79 dd (7, 1.15) | 15.9 | 2, 3 | | 1.75 d (6.85) | 16.25 | 2, 3 | 2 |
| 2 | 6.94 dq (7.5, 1.15) | 140.3 | 1, 4, 20 | | 6.98 q (6.9) | 140.79 | 4, 20 | |
| 3 | — | 130.3 | | | — | 130.3 | | |
| 4 | 6.06 brs | 125.5 | | 6 | 6.22 brs | 128.17 | 0 | |
| 5 | — | 139.1 | | | — | 138.1 | | |
| 6 | 6.37 m | 137.1 | 8 | 4 | 6.61 d (15.45) | 142.12 | 7, 8 | 3 |
| 7 | 6.35 m | 129.3 | | 10, 22 | 6.44 dd (15.45, 14.9) | 128.5 | | 9, 22 |
| 8 | 6.31 m | 134.8 | | | 6.84 dd (14.3, 14.85) | 143.45 | | 10 |
| 9 | 6.46 m | 128.8 | 8, 10 | 23 | 6.68 dd (14.3, 10.3) | 128.1 | 7 | 7, 23 |
| 10 | 6.25 d (11.4) | 129.3 | 12, 23 | 7, 12 | 7.53 d (11.45) | 145.44 | | 8, 13 |
| 11 | — | 134.2 | | | — | 134.2 | | |
| 12 | 4.81 s | 71.05 | 10, 11, 23, 23 | 10 | — | 198.85 | | |
| 13 | — | 61.5 | | | 4.37 d (5.75) | 49.13 | | 14 |
| 14 | 3.83 d (2.3) | 62.4 | 15 | | 2.34 brs | 39.8 | | 13, 18 |
| 15 | — | 85.3 | | | — | 86.69 | | |
| 17 | — | 171.7 | | | — | 171.04 | | |
| 18 | 2.02 m | 35.8 | | | 2.03 m | 41.49 | | 19 |
| 19a | 3.87 m | 58.4 | | | 3.85 m | 58.76 | | 18 |
| 19b | 3.99 m | 58.4 | | | 4.06 mm | 58.76 | | 18 |
| 20 | — | 167.9 | | | — | 167.57 | | |
| 21 | 3.72 s | 51.7 | 20 | | 3.74 s | 52.12 | 20 | |
| 22 | 1.66 s | 14.5 | 4, 5, 20 | 7 | 1.73 s | 14.25 | 4, 5, 6 | 7 |
| 23 | 1.83 s | 13.2 | 11, 12 | 9 | 1.98 s | 11.9 | 10, 11 | 9 |
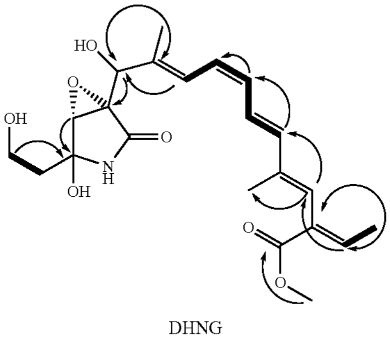
DHNG
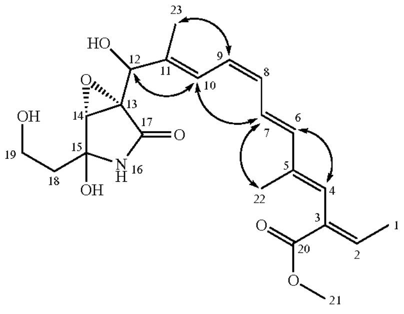

TABLE 1-continued

| | DHNG (1) | | | | DHLC-1 (2) | | | |
|---|---|---|---|---|---|---|---|---|
| No. | $\delta_H$ (Multiplicity, J Hz) | $\delta_C$ Type | HMBC | NOESY | $\delta_H$ (Multiplicity, J Hz) | $\delta_C$ Type | HMBC | NOESY |

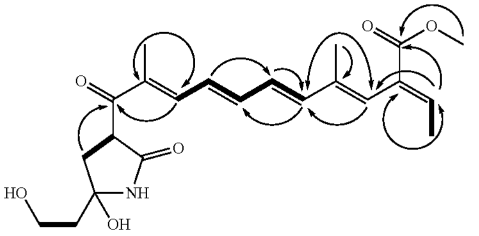

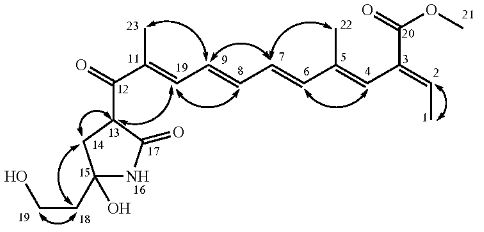

DHLC (Example 2) Production of the Compound of the Present Invention by Chemical Synthesis A method for producing lucilactaene using *Fusarium* sp. RK97-94 strain is disclosed in many documents including Patent Literature 1. A method of totally synthesizing lucilactaene is also disclosed in Non Patent Literatures 2 to 5.

The compound (DHLC) represented by formula (I) can be obtained by converting a compound obtained during the process for totally synthesizing lucilactaene in accordance with a method known in the art. Thus, DHLC can be totally synthesized without using the microorganism as mentioned above.

Specifically, lucilactaene was synthesized from 2-hydroxypyran as a starting substance in accordance with a synthesis method disclosed in Non Patent Literatures 2 to 5 and documents cited therein.

More specifically, t-Bu ester (compound 15 shown below) was synthesized from 2-hydroxypyran, subjected to an aldol reaction with acetaldehyde and a dehydration reaction, and totally trans-isomerized with a base. In this manner, triene (compound 17 shown below) having a desired stereochemistry (E,E,E) was selectively synthesized.

Further, IBX (Iodoxy Benzoic Acid) oxidation was carried out to obtain α,β-unsaturated aldehyde. Subsequently, the Horner-Emmons reaction was carried out to stereoselectively synthesize 5 consecutive olefins. With the ester (compound 19 shown below) obtained, a lithium salt of acetonitrile was reacted at a low temperature to selectively convert methyl ester to β-ketonitrile (compound 20 shown below). Further, t-Bu ester was induced into methyl ester to synthesize β-ketonitrile (12) having pentaene.

Scheme 3

[Formula 5]

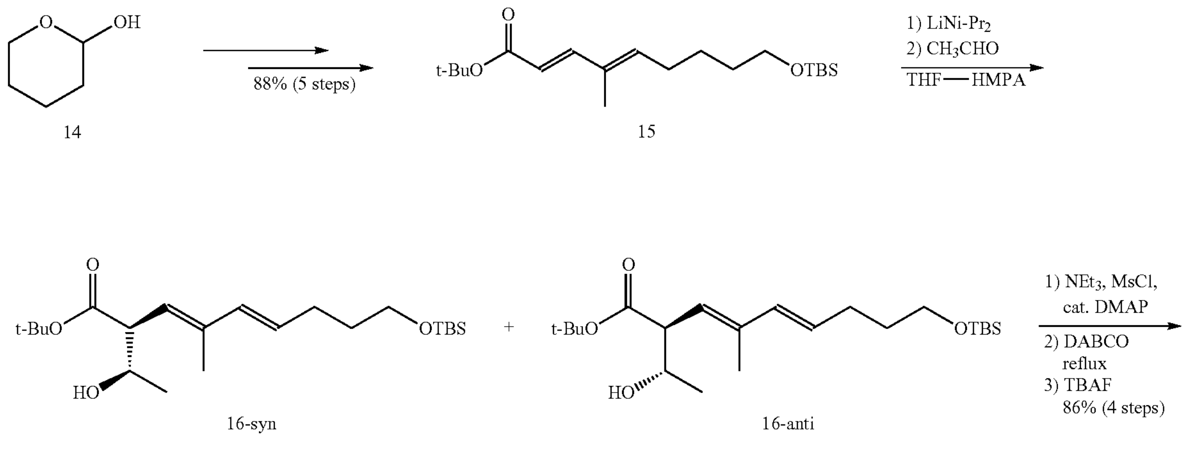

14
15
16-syn
16-anti

E,E-selective syn:anti = 1:1.6

-continued

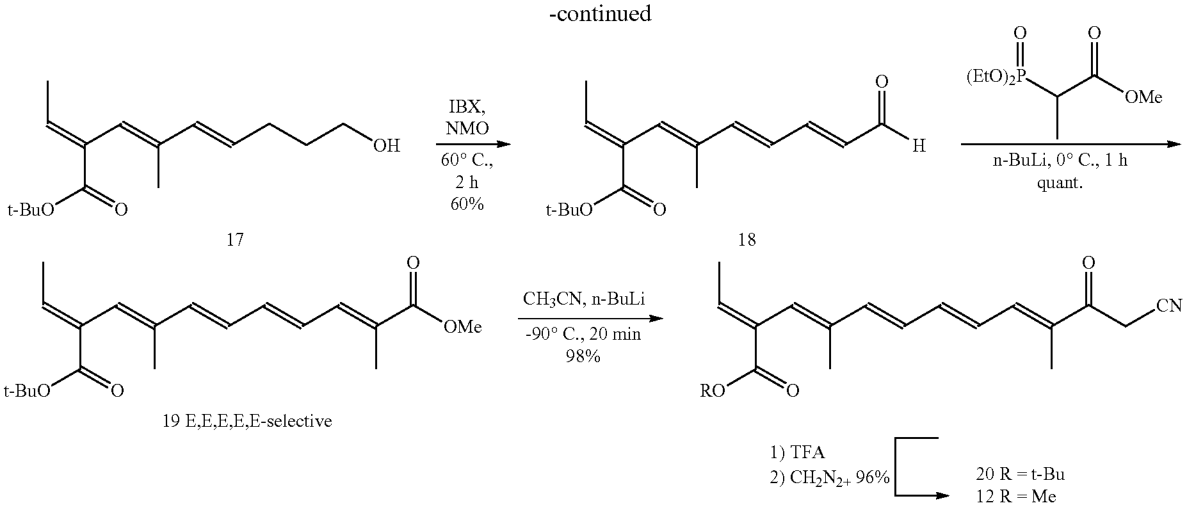

17

18

19 E,E,E,E,E-selective

20 R = t-Bu
12 R = Me (excerpt from "Scheme 3" of Non Patent Literature 5, P26)

Subsequently, the Knoevenagel reaction between pentaene (compound 12 shown below) obtained and optically active aldehyde (compound 13 shown below) was allowed to proceed to E-selectively obtain olefin (compound 21 shown below). Subsequently, stereoselective epoxidation was carried out, and then, a TES group was removed to obtain hydroxynitrile (compound 22 shown below). The hydroxynitrile (compound 22 shown below) is hydrolyzed by an intramolecular hydroxyl group on TLC (silica gel) and can be converted into lactone (compound 23 shown below). The lactone (compound 23 shown below) was amidated; oxidation of a hydroxyl group, formation of a lactam and removal of a TBDPS group were carried out to synthesize NG-391.

Further, with NG-391, TsOH in MeOH was reacted to stereo-selectively introduce methyl ether. Subsequently, an amide was protected with Boc to obtain compound 25 shown below as a single product. With compound 25, samarium iodide was reacted to obtain compound 26 shown below having an epoxy alone selectively reduced.

If lucilactaene is desired by synthesis, trifluoroacetic acid (TFA) is subsequently reacted with compound 26, and then, removal of a protecting group followed by stereoselective intramolecular Michael reaction is carried out. In this manner, a methyl ether form (compound 27 shown below) in a ratio of 55% and lucilactaene in a ratio of 28% can be synthesized separately as single diastereomers.

Scheme 4

[Formula 6]

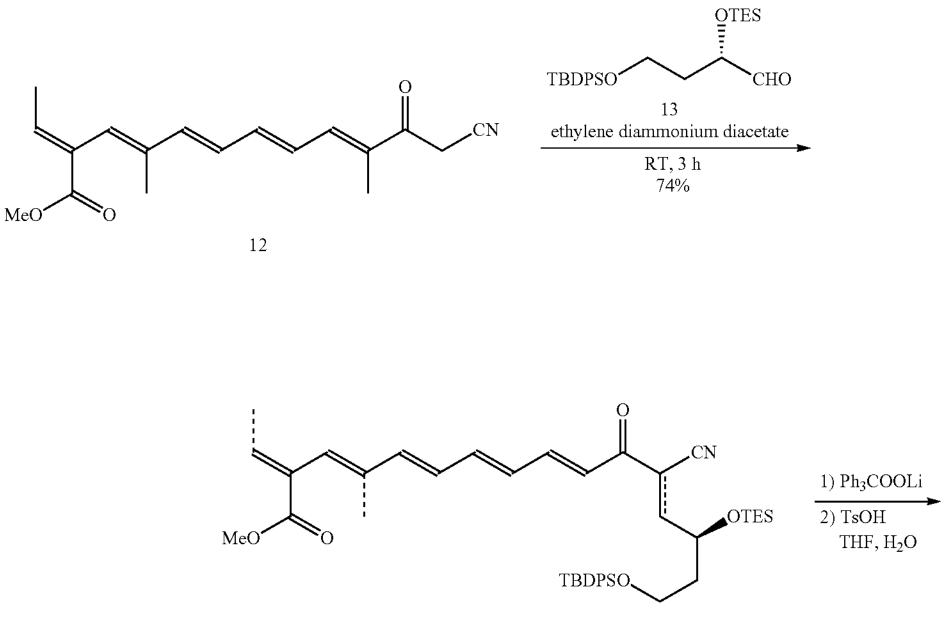

12

13

21

-continued
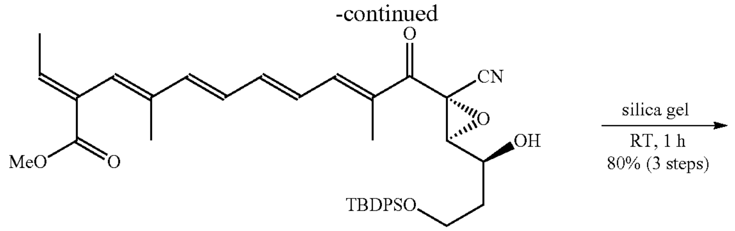
22
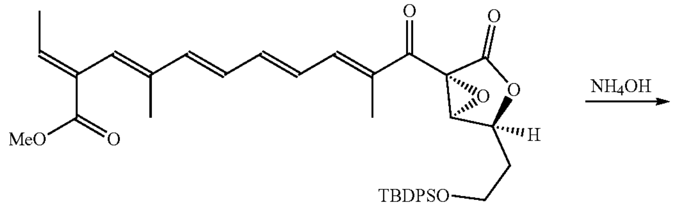
23
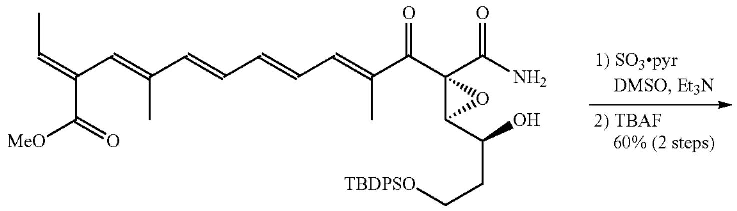
24
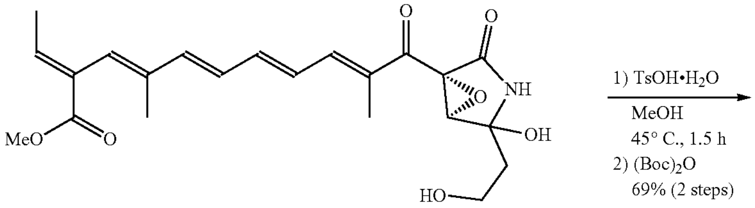
NG-391 (2)
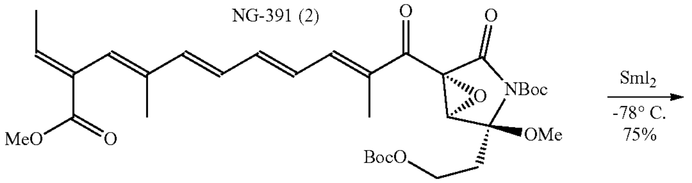
25
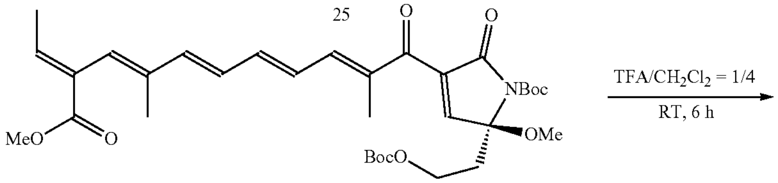
26
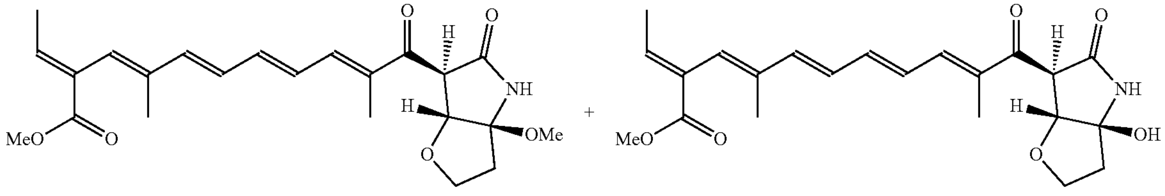
27
55%
$[\alpha]_D^{17}$ + 36.6 (*c* 0.17, MeOH)
lucilactaene (1) 28%
$[\alpha]_D^{20}$ 0 (*c* 0.1, MeOH)
lit. $[\alpha]_D^{20}$ 0 (*c* 0.1, MeOH)
(excerpt from "Scheme 4" of Non Patent Literature 5, P27)

In contrast, compound 26 obtained during a total synthesis process for lucilactaene was converted in the following scheme to obtain DHLC.

[Formula 7]

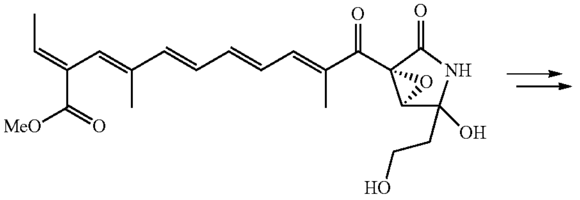

NG-391

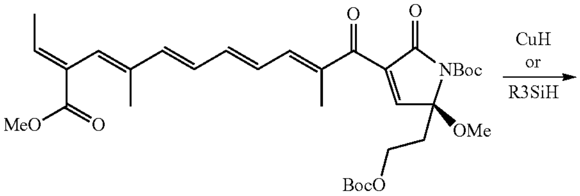

26
Angew. Chem. Int. Ed.
2005, 44, 3110

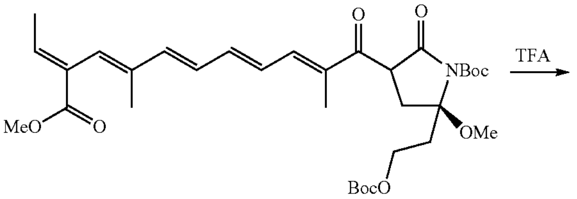

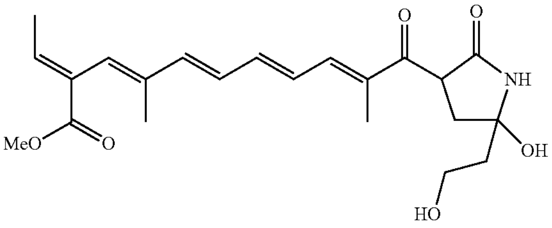

DHLC

-continued

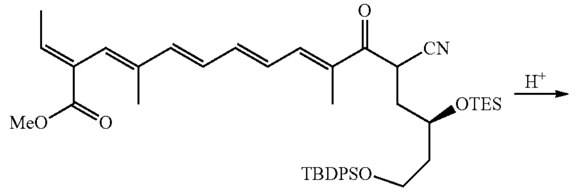

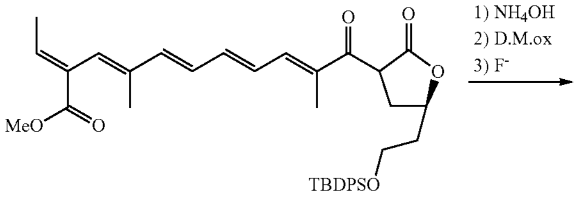

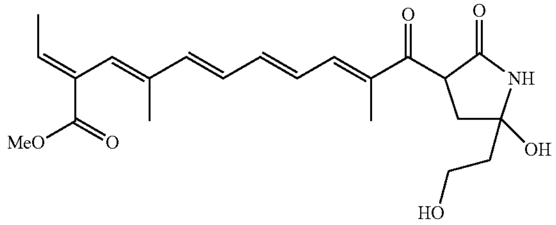

DHLC (see "Scheme 4" in Non Patent Literature 3, P9841)

Alternatively, DHLC was successfully obtained by converting compound 17 (shown below), which is an intermediate in the total synthesis process for NG-391 and illustrated in "Scheme 4" in Non Patent Literature 3, (P9841), in accordance with the following scheme.

[Formula 8]

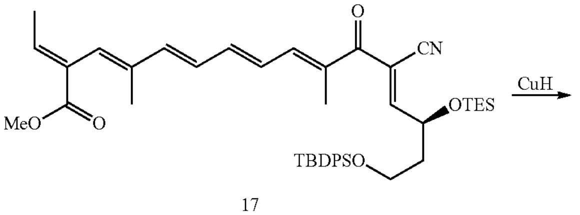

17
Tetrahedron, 2002, 58, 9839

(Example 3) Evaluation of Antimalarial Activity and Cytotoxicity

(1) Confirmation of Antimalarial Activity

In 2020, the present inventors reported that lucilactaene is a useful antimalarial compound ($IC_{50}$=0.063 μg/ml) in a paper (Non Patent Literature 1). Lucilactaene was found to exhibit an antimalarial effect about 12 times as high as compound NG-391 ($IC_{50}$=0.75 μg/ml) known in the art and having an analogous structure. The present inventors conducted studies on the antimalarial activity of DHLC based on the finding and found usefulness of DHLC.

Specifically, first, a wild-type malarial parasite, *Plasmodium falciparum* (pf3D7 strain) was cultured in a human type-A Rh+ erythrocyte-containing solution prepared such that the hematocrit level was 3% in a hypoxic condition ($O_2$ concentration: 5%, $CO_2$ concentration: 5%). A culture medium used herein was a complete medium (Gibco, RPMI 1640 medium) containing 25 mM N-(2-hydroxyethyl)piperazine-N'-2-ethanesulfonic acid (HEPES), 10 mg/mL hypoxanthine, 0.2 g/mL glucose, 5 μg/mL gentamicin and 10% bovine serum albumin.

Thereafter, DHLC solutions having 16 different concentrations within the range of 0.015 nM to 500 nM as shown in Table 2 were prepared using dimethyl sulfoxide (DMSO). Subsequently, to each of the wells of a 96 well microplate, 100 μl of a culture solution containing *Plasmodium falciparum* (pf3D7 strain) cultured in accordance with a method as mentioned above, was added, and then, 0.5 μl of a DHLC solution different in concentration was added to each well. Three sample sets were prepared in the same manner by adding 16 DHLC solutions different in concentration to wells, and then, allowed to stand still at 37° C. for 72 hours to expose *Plasmodium falciparum* (pf3D7 strain) to DHLC. Note that, each well contains the complete medium (RPMI medium), and the malarial parasite concentration was 0.3% and hematocrit level was 2%.

Thereafter, the 96 well microplates containing samples were frozen at −80° C. overnight, and then, thawed at room temperature to hemolyze red blood cells. Lactate dehydrogenase (pLDH), which is an intracellular metabolic enzyme of malarial parasite, in the samples contained in individual wells, was stained with a Malstat reagent (Flow Inc.) in accordance with the protocol of Malstat analysis (Am. J. Trop. Med. Hyg. 48(6), 1993, pp. 739-741) known in the art and the absorbance thereof was measured at 620 nm. Based on the results, the infection rates (%) of cells with malarial parasite, at different concentrations of DHLC were calculated.

In the same manner as above, the activity of DHLC was examined by use of drug-resistant *Plasmodium falciparum* (K1) resistant to an existing antimalarial drug, chloroquine.

Note that, a positive control used herein was a sample prepared by adding a solution prepared by diluting an existing antimalarial drug, i.e., chloroquine diphosphate, with distilled water, to wild-type *Plasmodium falciparum* (pf3D7 strain). A negative control used herein was a sample prepared by adding a solution prepared by diluting DMSO with distilled water, to a wild-type *Plasmodium falciparum* (pf3D7 strain). For measuring a background value, an erythrocyte-containing solution not infected with *Plasmodium falciparum*, was used.

The results are shown in Table 2 and FIG. 1.

TABLE 2

| | Concentration (nM) | | | | | | | |
|---|---|---|---|---|---|---|---|---|
| | 0.015 | 0.03 | 0.06 | 0.12 | 0.24 | 0.49 | 0.98 | 1.95 |
| pf3D7(%) | 98.9 | 109.8 | 89.4 | 92.9 | 77.2 | 74.1 | 41.7 | 28.2 |
| | Concentration (nM) | | | | | | | |
| | 3.90 | 7.81 | 15.63 | 31.25 | 62.5 | 125 | 250 | 500 |
| pf3D7(%) | 22.9 | 23.7 | 13.3 | 9.6 | 14.3 | 10.2 | 8.5 | 13.9 |

The growth inhibitory activity ($IC_{50}$ value) of each of the *Plasmodium falciparum* was confirmed based on the data obtained above. As a result, it was found that DHLC has extremely high activity ($IC_{50}$=0.65 nM (0.00026 μg/ml)) on wild-type *Plasmodium falciparum* (pf3D7 strain) (Table 2). It was also found that DHLC has antimalarial activity against a drug-resistant *Plasmodium falciparum* (K1) as high as against wild-type *Plasmodium falciparum* (FIG. 1). From this, it was demonstrated that DHLC has antimalarial activity, which is 1000 times or more as high as NG-391 ($IC_{50}$=0.75 μg/ml) already reported by the present inventors and about 100 times or more as high as lucilactaene ($IC_{50}$=0.063 μg/ml).

(2) Evaluation of Cytotoxicity

Subsequently, the cytotoxicity of DHLC was examined. More specifically, the activity of DHLC to various types of cancer cells (Hela cells, HL-60 cells, MKN74 cells, NB-1 cells, T98G cells) were examined. The growth inhibitory activities ($IC_{50}$ value) against the individual cells are shown in Table 3 (unit: μg/ml).

The cytotoxic activity of DHLC to Hela cells was $IC_{50}$=21 μg/ml, that to HL-60 cells was $IC_{50}$=3.4 μg/ml, and that to NB-1 cells was $IC_{50}$=0.34 μg/ml. In contrast, the cytotoxicity of DHLC to MKN74 cells and T98G cells were as low as $IC_{50}$>30 μg/ml.

From the above, it was found that the compound of the present invention has high antimalarial activity and can be used as an antimalarial drug applicable to living bodies.

TABLE 3

| Type | Cell line/Strain | Lucilactaene | NG-391 | Demethyl lucilactaene | DHLC |
|---|---|---|---|---|---|
| Cancer cells | HeLa | 10 | 5.9 | >30 | 21 |
| | HL-60 | 7 | 6.6 | >30 | 3.4 |
| | MKN74 | | | | >30 |
| | NB-1 | | | | 0.34 |
| | T98G | | | | >30 |

All publications, patents, and patent applications cited herein are incorporated herein by reference in their entirety.

The invention claimed is:

1. A compound represented by the following formula (I):

(I)

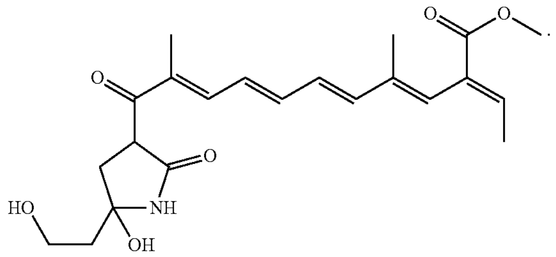

2. A method for treating malaria in a subject in need thereof, comprising administering to the subject an effective amount of the compound according to claim 1.

* * * * *